United States Patent [19]

Bloom, deceased et al.

[11] 4,267,254
[45] May 12, 1981

[54] PHOTOGRAPHIC PROCESS

[75] Inventors: Stanley M. Bloom, deceased, late of Waban, Mass., by Arlene N. Bloom, executrix; Krishna G. Sachdev, Cambridge, Mass.

[73] Assignee: Polaroid Corporation, Cambridge, Mass.

[21] Appl. No.: 80,349

[22] Filed: Oct. 1, 1979

[51] Int. Cl.$^3$ .................. G03C 5/54; G03C 7/00; G03C 5/38
[52] U.S. Cl. .................. 430/245; 430/251; 430/428; 430/455
[58] Field of Search .............. 430/245, 246, 251, 428, 430/455

[56] References Cited

U.S. PATENT DOCUMENTS

| | | | |
|---|---|---|---|
| 3,062,646 | 11/1962 | Dann et al | 430/600 |
| 3,930,867 | 1/1976 | Bigelow | 430/600 |
| 3,975,423 | 8/1976 | Borror et al. | 430/251 |
| 4,017,314 | 4/1977 | Blake | 430/485 |
| 4,168,166 | 9/1979 | Land | 430/245 |

OTHER PUBLICATIONS

Pelissard et al., *Tetrahedron Letters,* vol. 45, 1972, pp. 4589–4592.

Louis et al., *Inorganic Nuclear Chem. Letters,* vol. 13, 1977, pp. 31–35.

*Primary Examiner*—Richard L. Schilling
*Attorney, Agent, or Firm*—Gaetano D. Maccarone

[57] ABSTRACT

There is described a photograhic method employing a positive-negative diffusion transfer film unit wherein there is formed a positive silver transfer image which may be viewed as a positive transparency without being separated from the developed negative silver image, including an embodiment wherein additive color projection positive images are formed. According to the method, the exposed film unit is developed by contacting the silver halide emulsion layer with a photographic processing composition which comprises an aqueous alkaline solution containing a silver halide developing agent and a silver complexing agent. The silver complexing agent is stable in an alkaline environment, has a melting point less than about 50° C. preferably about 25° C. or less, and the log of the stability constant ($\beta$) for a 1:1 complex of the complexing agent with silver is at least about 10.5. The film unit is not washed during the method. According to the method of the invention crystal formation in the transparency is substantially or completely eliminated.

15 Claims, No Drawings

PHOTOGRAPHIC PROCESS

BACKGROUND OF THE INVENTION

This application relates to a photographic diffusion transfer method and, more particularly, to such a method wherein there are utilized silver complexing agents having advantageous properties.

The use of silver complexing agents, also referred to as "silver halide solvents", in diffusion transfer photographic methods is known in the art. In methods of this type an exposed silver halide emulsion is developed by contacting it with a photographic processing composition whereby an imagewise distribution of diffusible image forming components is formed in the unexposed and undeveloped areas of the silver halide. This imagewise distribution of image forming components is transferred to an image receiving stratum which is in superposed relationship with the silver halide emulsion layer to provide the desired transfer image.

In diffusion transfer methods wherein a silver transfer image is formed, the method is carried out in the presence of a silver complexing agent which forms a soluble and diffusible complex with undeveloped silver halide. The soluble silver complex which is formed diffuses to the superposed image receiving layer where metallic silver is deposited to provide the desired silver transfer image.

Various materials have been taught as being useful as silver complexing agents in positive-negative diffusion transfer photographic methods. Among these are thiosulfates, such as potassium and sodium thiosulfate; thiocyanates such as potassium and sodium thiocyanate; cyclic amides such as barbituric acid and uracil; 1,1-bis-sulfonyl alkanes such as are disclosed in U.S. Pat. No. 3,769,014; and alkylthioalkyl-substituted alkylsulfonylacetonitriles such as are disclosed in U.S. Pat. No. 3,975,423. These materials have been found to be suitable for performing their intended functions. Nevertheless, they are not completely satisfactory in every type of positive-negative diffusion transfer film unit wherein a silver transfer image is formed.

For example, there are known, in the art, diffusion transfer methods which are adapted to provide positive silver transfer images which may be viewed as positive transparencies without being separated from the developed negative silver image, including methods for forming additive color positive images which are viewed by projecting the transparency on a viewing surface. The film units employed in such methods are retained intact during processing and are not washed. Accordingly, the silver complexing agent, which typically may comprise from about 3 to about 15 percent by weight of the photographic processing composition, remains in the image receiving layer where the silver transfer positive image is formed. Because of factors such as the amount of the silver complexing agent present in the film unit and the physical properties of the known silver complexing agents, many of which have relatively high melting points, the known complexing agents tend to form crystals within a relatively short time, e.g., as brief as a day after formation of the image. Such crystal formation is undesirable because it detracts from the aesthetic quality of the image and in the case of projection transparencies adversely affects the quality of the projected image for viewing.

Thus, it would be desirable to provide a diffusion transfer method of this type wherein crystal formation in the positive silver transfer image is substantially or completely eliminated. The present application is drawn to such a method.

SUMMARY OF THE INVENTION

It is, therefore, the object of this invention to provide a novel photographic diffusion transfer method.

It is another object to provide a method which provides positive silver transfer images which may be viewed as positive transparencies without being separated from the developed silver negative image.

It is a further object to provide a method for forming additive color positive images which are viewed by projection upon a viewing surface without being separated from the developed negative silver image.

Still another object is to provide a photographic diffusion transfer method wherein the film unit is not washed during processing.

It is yet another object of the invention to provide a diffusion transfer method which utilizes silver complexing agents having physical properties such that the formation of crystals in the positive silver transfer image is substantially or completely eliminated.

BRIEF SUMMARY OF THE INVENTION

These and other objects and advantages are accomplished in accordance with the invention by providing a photographic method employing a positive-negative diffusion transfer film unit wherein there is formed, without washing, a positive silver transfer image which may be viewed as a positive transparency without being separated from the developed negative silver image. According to the method, the exposed film unit is developed by contacting the silver halide emulsion layer with a photographic processing composition which comprises an aqueous alkaline solution containing a silver halide developing agent and a silver complexing agent. The silver complexing agent is stable in an alkaline environment, has a melting point of less than about 50° C., preferably about 25° C. or less, and the log of the stability constant ($\beta$) for a 1:1 complex of the complexing agent with silver is at least about 10.5. The preferred silver complexing agents are liquids at room temperature.

By "stable in alkaline environment" as used in the present application is meant that the complexing agent retains at least 75% of its silver complexing ability after being in a 1N sodium hydroxide solution for twenty-four hours at room temperature.

It has been found that the use of such silver complexing agents, because of their physical properties, contributes to the substantial or complete elimination of crystal formation in the transparency. Consequently, such silver complexing agents may be used in the amounts typically required to effect rapid and substantially complete transfer of the positive silver transfer image forming components to the image-receiving layer while at the same time substantially or completely eliminating the difficulties with crystal formation which have been encountered heretofore. Further, it has been found that silver complexing agents having the specified physical properties may be used in combination with other silver complexing agents which do not possess all of the same properties to provide the advantageous results which are obtained according to the method of the invention.

DESCRIPTION OF THE PREFERRED EMBODIMENTS

A positive-negative diffusion transfer film unit which may be utilized in the method of the invention comprises a transparent support such as, for example, an organic polymeric material, carrying a photosensitive silver halide emulsion layer and an image-receiving layer. In a preferred embodiment the film unit includes a multicolor additive screen, preferably a three color screen such as one having alternating red, blue and green lines. These film units can be fabricated by techniques which are known in the art. A technique for fabricating a transparent support carrying a pattern of alternating, microscopically fine, red, blue and green lines is described in U.S. Pat. No. 3,284,208. Deposition of a silver halide emulsion layer and an image receiving layer can be effected by any of many techniques. The silver halide may be a silver chloride, iodide, bromide, iodobromide, chlorobromide, etc. The binder for the halide, though usually gelatin, may be any suitable polymer such as polyvinyl alcohol, polyvinyl pyrrolidone and their copolymers. The image receiving layer preferably includes certain materials the presence of which during the transfer process has a desirable effect upon the amount and character of the silver precipitated on the layer. Specific materials of this type are known in the art. The film unit optionally may include other layers such as an antihalation layer as will be apparent to those skilled in the art.

As mentioned previously, in operation of the method the exposed silver halide emulsion layer is developed by being contacted with a photographic processing composition which includes a silver halide developing agent and a silver complexing agent having the properties described above. There is thus formed in the unexposed and undeveloped areas of the silver halide emulsion layer a soluble and diffusible complex of the silver complexing agent and silver. This imagewise pattern of the complex is transferred to the image-receiving layer which is in superposed relationship with the silver halide emulsion layer and there is provided in the former the desired positive silver transfer image.

The silver complexing agents which have the specified physical properties include cyclic and acyclic compounds. Specific suitable cyclic crown ether silver complexing agents are represented by the following structural formulas:

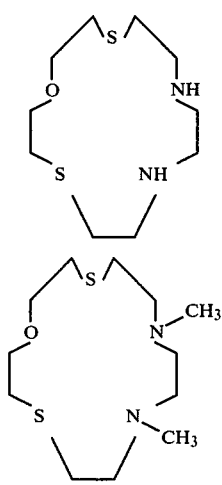

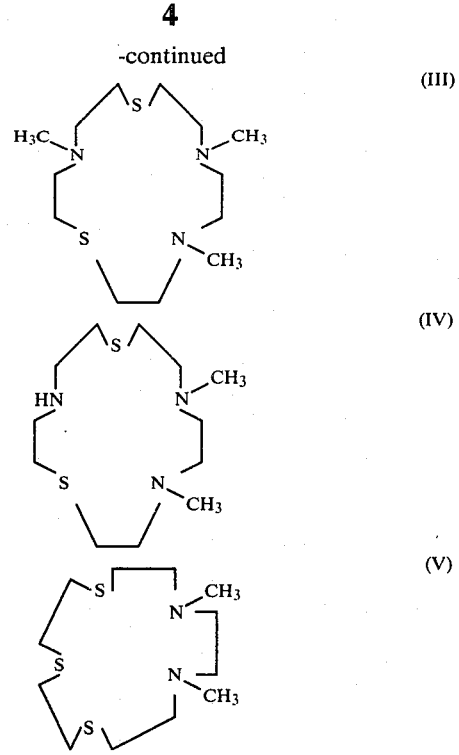

Specific suitable acyclic silver complexing agents are represented by the following structural formulas:

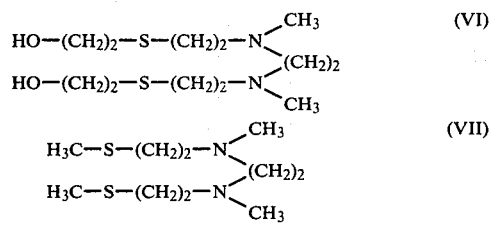

Compound (I) is disclosed in Tetrahedron Letters, Pelissard and Louis, 45, pp 4589–4592 (1972). The other compounds are per se novel compounds and are disclosed and claimed in applicants' copending applications Ser. No. 080,440 and Ser. No. 080,350, both filed on even date herewith.

Compound (I) may be synthesized according to the method described in the above-cited literature article. Alternatively, the novel 15 crown —5 ligands may be synthesized by reacting N,N'-dimethyl-N,N'-bis (2-mercaptoethyl)ethylenediamine [for its preparation see J.Amer.Chem.Soc., 98, 6951(1976)] with (ClCH$_2$CH$_2$) X (where X may be O, S, NH or N—Me) in a suspension of sodium hydride in dimethylformamide. Compounds (VI) and (VII) can be made by reacting the ethylenediamine compound with ethylene oxide and methyl iodide respectively. The desired ligands can be separated from the crude reaction products by first treating a methanol solution of the roduct with silver thiocyanate to form a 1:1 ligand-silver thiocyanate complex which preferentially crystallizes from solution while the impurities remain in the filtrate. Recrystallization of the complex followed by the precipitation of silver as silver sulfide with hydrogen sulfide and liberation of the free ligand by passing an aqueous solution of the resulting thiocyanic acid complex through an anion exchange column provides essentially pure samples of the ligands. Alternatively, purification can be effected by chromatography of the crude product mixture on silica gel, a more time consuming procedure.

As mentioned previously, for the silver complexing agents utilized in the method of the invention, the log of the stability constant ($\beta$) for a 1:1 complex of the complexing agent with silver is at least about 10.5. The log of the stability constant ($\beta$) for each of the specific preferred silver complexing agents employed in the method is shown in Table I. The stability constants were determined by potentiometry, i.e., by titrating the ligand with a standardized solution of silver perchlorate in mildly alkaline, and constant ionic strength medium (0.05 M NaOH, 0.10 M NaClO$_4$). All solutions and titrants were prepared carbonate free and with an ionic strength of 0.1 M(NaClO$_4$) except when the perchlorate salt of the complex was found to be insoluble. In that eventuality perchlorate was omitted from the system. An argon atmosphere was used throughout. The indicating electrode was a silver specific ion type used in conjunction with a sleeve type double junction Ag-/AgCl reference electrode.

TABLE I

| Compound | log |
| --- | --- |
| I | 11.37 ± .01 |
| II | 11.84 ± .01 |
| III | 12.30 ± .01 |
| IV* | 11.98 ± .02 |
| V | 11.84 ± .02 |
| VI | 10.91 ± .01 |
| VII | 10.97 ± .01 |

*No perchlorate was added.

The photographic processing composition which is utilized according to the method of the invention may include one or more of the silver complexing agents having the properties specified above. The total amount of silver complexing agent(s) present in the processing composition in any specific instance may vary depending upon factors such as, for example, the particular materials which comprise the respective elements of the film unit and the particular processing conditions which are employed. Generally, the total amount of the silver complexing agent(s) present in the processing composition is in the range of from about 1 percent to about 10 percent by weight of the composition.

It has also been found through laboratory experimentation that the silver complexing agents of the type described above can be used together with silver complexing agents which do not possess the specified melting point and silver complexing ability and continue to provide the advantageous results obtained according to the present method. It has been shown that silver complexing agents which do not possess the specified properties and which, when used alone in the amounts necessary for processing quickly form crystals in the transparency, can be combined with the silver complexing agents having the specified physical properties, utilized under the same processing conditions and yet provide transparencies wherein crystal formation is substantially or completely eliminated. It has been found that molar equivalent amounts of the respective types of silver complexing agents can be used together and provide the advantageous results obtained according to the invention.

The photographic processing composition, in addition to the silver complexing agent(s) of the requisite type, comprises a suitable silver halide developing agent, preferably an organic developing agent. Examples of developing agents that may be used include hydroquinone and substituted hydroquinones such as tertiary butyl hydroquinone, 2,5-dimethyl hydroquinone, ethoxyhydroquinone and chlorohydroquinone; pyrogallol and catechols such as catechol, 4-phenyl catechol and tertiary butyl catechol; aminophenols such as 2,4,6-triaminoorthocresol, 1,4-diaminobenzenes such as p-phenylenediamine; 1,2,4-triamino-benzene; 4-amino-2-methyl-N-N-diethylaniline, ascorbic acid and its derivates such as ascorbic acid, isoascorbic acid and 5,6-isopropylidene ascorbic acid; other enediols such as tetramethyl reductic acid; and hydroxylamines such as N,N-di-(2-ethoxyethyl) hydroxylamine and N,N-di-(2-methoxyethoxyethyl) hydroxylamine.

It should be noted that the relative proportions of the silver complexing agent(s) and the other components of the processing composition may be varied to suit the requirements of any particular film unit and processing conditions employed according to the present method. In addition, it will be apparent that where desirable there may be included in the processing composition other components as are commonly utilized in the photographic art, such as antifoggants, etc.

In diffusion transfer processes, the processing composition, if it is to be applied to the emulsion by being spread thereon in a thin layer, usually also includes a viscosity imparting reagent. Thus the processing composition employed in the method may comprise, for example, one or more of the silver complexing agents having the specified properties, one or more of the conventional developing agents such as those described above, an alkali such as sodium hydroxide or potassium hydroxide and a viscosity imparting reagent such as a high molecular weight polymer, for example, sodium carboxymethyl cellulose or hydroxyethyl cellulose.

In one embodiment the processing composition is applied in a uniformly thin layer between the superposed surfaces of the silver halide emulsion layer and the image receiving layer by advancing the film unit between a pair of pressure applying rollers.

As noted previously, in diffusion transfer film units the negative component which comprises at least one photosensitive silver halide emulsion layer and the positive component which comprises an image receiving layer may be in separate sheet-like elements which are brought together during processing and thereafter retained together as a permanent laminate according to the present method or the negative and positive components may be initially provided in the same integral element. In the latter type of film unit, typically, the image receiving layer is coated upon a support and the photosensitive layer is deposited upon the surface of the image-receiving layer.

The invention will now be described further in detail with respect to specific preferred embodiments by way of examples, it being understood that these are illustrative only and the invention is not intended to be limited to the materials, conditions, process parameters, etc., which are recited therein. All parts and percentages are by weight unless otherwise indicated.

EXAMPLE I

Preparation of N,N'-dimethyl-N,N'-bis(2-mercaptoethyl)ethylene diamine

A 250 ml three-neck flask, equipped with a magnetic stirrer, addition funnel, thermometer and argon inlet was charged with a solution of 18.3 g. (0.208 mol) of N,N'-methylethylenediamine in 70 ml of benzene. A solution of 25.1 g. (0.417 mol) of ethylene sulfide in 10 ml of benzene was added with stirring to the solution in the flask under argon while maintaining the temperature of the solution in the flask at 50°–55° C. The resulting clear solution was allowed to remain overnight at ambient temperature, washed with two 5 ml portions of water and dried over magnesium sulfate. The solvent was removed under reduced pressure and 39.9 g. (97% yield) of a colorless oil was obtained.

The material is susceptible to air oxidation and therefore further purification was not carried out. The material can be stored up to a week under argon in a freezer without any significant deterioration. Since the compound has an extremely unpleasant odor and can cause severe skin allergy careful handling is necessary.

Preparation of Compound (II)

A three neck one liter flask equipped with an overhead stirrer, addition funnel and argon inlet, and an oil bath was charged with 14.5 g. of a 50% sodium hydride dispersion in oil (0.26 mol of NaH). Most of the oil was removed by repeated washings with petroleum ether carrier out under argon. In each washing about 15-20 ml of petroleum ether were added to the dispersion, the dispersion stirred briefly and allowed to settle and supernatant liquid removed with a syringe. 520 ml of spectrograde dimethylformamide were then introduced into the dispersion and the reaction flask was heated with the oil bath maintained at about 95° C. When the internal temperature of the flask reached about 75° C. there was begun the dropwise addition, with vigorous stirring, of a mixture of 27.08 g. (0.13 mole) of N,N'-dimethyl-N,N'-bis(2-mercaptoethyl) ethylenediamine and 18.6 g. (0.13 mole) of bis-2-chloroethylether in 40 ml dimethylformamide. Addition of the mixture was completed in 2.5 hours with the temperature maintained between 80°–85° C. throughout the addition of the mixture and for about 16 hours thereafter. Most of the solvent was removed in vacuo with the bath temperature at about 70°–75° C. The resulting thick light brown oil was dissolved in 300 ml of ethylacetate, washed with three 20 ml portions of water and dried over magnesium sulfate. Removal of the solvent under reduced pressure gave 34 g. of a light brown syrup. Analysis showed this to be a complex mixture of products.

A solution of 18 g. of the crude product in 200 ml of methanol was formed and to it there were added 10.9 g. of silver thiocyanate in portions. Toward the end of the silver thiocyanate addition dissolution of the silver salt became slow and a sticky material separated from solution. The mixture was stirred for about 15 minutes after which the soluble portion was removed, diluted with 100 ml of methanol and filtered through Celite 542 (a diatomaceous earth material available from Johns Manville Co.). The filtrate was concentrated to 120 ml under reduced pressure and stored for two days in a refrigerator. Light yellow crystals deposited during storage and these were collected, washed with methanol and recrystallized from methanol twice at low temperature by first dissolving the crystals in excess solvent at 40° C. and then concentrating to about one-half the initial volume. The crystals were then dried under high vacuum. A total of 8.5 g. of 1:1 compound (II)—silver thiocyanate complex, m.p. 147°–149° C. was recovered. Recrystallization of a small sample of this material gave essentially colorless crystals, m.p. 149°–150° C. $C_{13}H_{26}N_3OS.Ag$ requires 35.13% C, 5.89% H, 9.46% N, 21.64% S and 24.27% Ag. Elemental analysis of this material gave 35.03% C, 5.91% H, 9.50% N, 21.60% S and 24.43% Ag. Also NMR spectral data were consistent with a 1:1 compound (II)—silver thiocyanate complex stoichiometry.

8.3 g. (18.7 moles) of the complex were dissolved in 100 ml of a 70:30 (vol/vol) mixture of dichloromethane and ether and treated with hydrogen sulfide gas to precipitate silver as silver sulfide. Bubbling of hydrogen sulfide was continued until an aliquot of the supernatant solution gave no precipate with hydrogen sulfide. The mixture was then stirred for about 15 minutes, filtered through Celite 542 and the filtrate was concentrated to a thick colorless syrup, presumably a thiocyanic acid complex of ligand (II). The free ligand, compound (II), was liberated from this material by the following alternative procedures:

(A) A column of a strongly basic, quaternary ammonium (polystyrene) type, anion exchange resin (Amberlite IRA-400) was prepared in carbonate-free water, washed with dilute sodium hydroxide and then throughly with water until the eluent was not basic. An aqueous solution of the colorless syrup was passed through the column and washing with carbonate-free water was continued until most of the material had been eluted. The combined washings were concentrated under reduced pressure. The residual syrup was dissolved in absolute ethanol, filtered through Celite 542 and the filtrate concentrated to provide about 5 g. of compound (II) as a clear colorless syrup. The sample was dried at 50° C. by pumping under high vacuum.

(B) Alternatively, the aqueous solution of the thiocyanic acid complex was treated with a stoichiometric amount of a 10% aqueous tetramethylammonium hydroxide solution and extracted with ethylacetate or dichloromethane. The organic layer was washed with water and dried over anhydrous sodium sulfate. Removal of the solvent gave compound (II) as a colorless syrup.

$C_{12}H_{26}N_2S_2O$ requires 51.75% C, 9.41% H, 10.06% N, and 23.03% S. Elemental analysis gave 51.74% C, 9.39% H, 10.02% N and 22.84% S.

A film unit was prepared as follows: the light-sensitive element comprised a transparent polyester film base carrying on one surface an additive color screen of approximately 1500 triplets per inch of red, blue and green filter screen elements in repetitive side by side relationship; a composite barrier structure made up of an approximately 0.7 micron thick layer of polyvinylidene chloride coated from a solvent, an approximately 1.0 micron thick layer of polyvinylidene chloride coated from water emulsion and an approximately 0.3 micron thick layer of polyvinyl formal; a nucleating layer comprising 0.23 mg./ft.$^2$ of palladium nuclei (as metal), ) 0.29 mg./ft.$^2$ of gelatin, 0.35 mg./ft.$^2$ of tin (as metal) and 0.47 mg./ft.$^2$ of total chloride (associated with Pd and Sn); an interlayer of 1.94 mgs./ft.$^2$ of gelatin, and 0.194 mg./ft.$^2$ of alkyl phenoxy polyoxy ethylene glycol; a hardened gelatino silver iodobromo emulsion coated at a coverage of about 85 mgs./ft.² of silver, 85 mgs./ft² of gelatin, 7.5 mgs./ft.² of propylene glycol alginate, 0.41 mg./ft.² of chrome alum (coverage as $K_2Cr(SO_4)_2$; and 0.61 mg./ft.² of alkyl phenol polyglycol ether (average 9.5 mols ethylene oxide) surfactant; and an antihalo top coat of 300 mgs./ft.² of gelatin, 175 mgs./ft.² of Dow 620 carboxylated styrene butadiene latex, 22 mgs./ft.² of propylene glycol alginate, 1.2 mgs./ft.² of dioctyl ester of sodium succinic acid, 5.6 mgs./ft.² of pyridinium bis-1,5(1,3-diethyl-2-thiol-5-barbituric acid) pentamethine oxanol, 7.0 mgs./ft.² of 4-(2-chloro-4-dimethylamino benzaldehyde)-1-(p-phenyl carboxylic acid)-3-methyl pyrazolone-5 and 5.0 mgs./ft.² of benzimidazole-2-thiol gold $Au^{+1}$ complex (as gold).

The cover sheet comprised a 4 mil thick polyester support having a thin coating on one surface to prepare the support for coating. Coated on the support in the following order were:

(A) An acid providing layer formed by combining 60 parts by volume of a 30% solution of the half butyl ester of ethylene maleic anhydride in methyl ethyl ketone and 40 parts by volume of a solution of 5.7% Butvar B-72 (available from Monsanto), 63.3% ethyl acetate and 31% n-butanol and coating the mixture on the support to provide a dry coverage of about 2.45 gms/ft²; and (B) A gelatin layer formed by coating a water solution containing 10% deionized gelatin, and 0.05% Emulphor ON-870 (available from Antara Chemical Co.) to provide a dry coverage of about 1 gm/ft².

The film unit as identified above was exposed to a step wedge and processed while being retained intact, by spreading a layer of a processing composition less than about 3 mils thick between the light-sensitive element and cover sheet. The processing composition was prepared by adding 0.5 ml of compound (II) to 10 ml of the following formulation:

| Water | 82.36 g. |
|---|---|
| Sodium hydroxide | 7.265 g. |
| Hydroxyethyl cellulose | 2.811 g. |
| Sodium sulfite | 2.54 g. |
| Tetramethyl reductic acid | 3.17 g. |
| Dodecyl-N,N-dipyridinium dibromide | 1.78 g. |
| 4-aminopyrzaolo (3,4-d) pyrimidine | 0.016 g. |
| 5-bromo-6-methyl-4-azabenzimidazole | 0.016 g. |
| Thiazololidine-2-thione | 0.035 g. |

After an imbibition period of about one minute, the resultant image was examined visually and found to be substantially free of crystals. After a period of 17 days, the image was again examined visually and again found to be substantially free of crystals. The transparency was stored under ambient conditions during the interim.

An identical film unit was processed in the same manner with the exception that the processing composition included 0.4061 g of a 2-alkylthioether-4,6-dihydroxypyrimidine complexing agent (approximate molar equivalent of 0.5 ml of compound II) in place of compound II. Crystals were visually apparent in the transparency within one day after processing.

Another film unit was processed in the same manner described above with the exception that the processing composition was made up of equal volumes of each of the processing compositions previously described in this example. The transparency, when examined visually immediately after processing and 17 days later, was found to be substantially free of crystals.

EXAMPLE II

Preparation of Compound (III)

To a suspension of 0.24 g. of a 50% sodium hydride dispersion in oil (which had previously been washed free of oil with petroleum ether) in 15 ml of dimethylformamide was added 0.95 g. of mechlorethamine hydrochloride. To the resulting free amine were added 1.05 g. of N,N'-dimethyl-N,N'-bis(2-mercaptoethyl) ethylenediamine in 5 ml of dimethylformamide.

To a separate three neck flask there was added 0.5 g. of a 50% sodium hydride dispersion in oil and this was washed free of oil with petroleum ether under argon. To this were added 50 ml of dimethylformamide and the suspension was heated to 80°–90° C. The mixture of the two reactants prepared above was then added dropwise with vigorous stirring over a period of about 25 minutes and stirring was continued at that temperature overnight. The solvent was then removed under reduced pressure, the residue taken up in 25 ml of ethyl acetate, washed twice with 5 ml portions of water and dried over sodium sulfate. Removal of the solvent gave 1.4 g. of a slightly colored syrup. $^{13}C$ NMR and thin layer chromatography on silica gel using a 50:50 (vol/vol) mixture of ethylacetate-hexane showed this to be a mixture of products. Purification by column chromatography on silica gel gave 0.5 g. of compound (III) characterized by $^{13}C$ NMR and mass spectrum (m/e=291, parent ion and 292, P+1).

A stirred solution of 116 mg of compound (III) in 5 ml methanol was treated with 66.4 mg of silver thiocyanate. After 10 minutes the mixture was filtered to remove traces of suspended material and the solvent removed under reduced pressure to give a white crystalline solid, m.p. 160°–162° C. The product was crystallized from methanol by storing for several days in a refrigerator. Needle-like crystals formed and these were collected by filtration and washed to give colorless needles, m.p. 164°–165° C.

$C_{14}H_{29}N_4S_3.AG$ requires 36.75% C, 6.39% H, 12.25% N, 21.03% S and 23.58% Ag. Elemental analysis of the product gave 36.70% C, 6.35% H, 12.29% N, 21.03% S and 23.74% Ag.

EXAMPLE III

Preparation of Compound (IV)

In a two-neck flask 0.24 g. of a 50% sodium hydride dispersion in oil was washed free of oil with petroleum ether under argon atmosphere and then 15 ml of dimethylformamide were introduced with a syringe. The suspension was stirred for 5 minutes and 0.89 g. of bis-chloroethylamine hydrochloride was added with stirring followed by the addition of 1.5 g. of N,N'-dimethyl-N,N'bis(2-mercaptoethyl) ethylenediamine.

In a separate 3-neck flask equipped with an addition funnel there was added 0.5 g. of a 50% sodium hydride dispersion in oil which was then washed free of oil with petroleum ether under argon. Then 45 ml of dimethylformamide were added and the suspension was stirred at a temperature of 80°–90° C. To the suspension was added dropwise over a period of about 1.5 hours the reactant mixture described above. Stirring was continued overnight at that temperature and then for an additional period at room temperature. Most of the solvent was removed under reduced pressure and the residue was taken up in 30 ml ethyl acetate, washed twice with 5 ml portions of water and dried over sodium sulfate. Removal of the solvent gave a clear light brown syrup.

The product was purified by column chromatography on silica gel using an ethyl acetate-ethanol mixture for elution. NMR spectra of the product were consistent with compound (IV).

EXAMPLE IV

Preparation of Compound V

In a 250 ml three neck flask equipped with an addition funnel, reflux condenser and a serum cap there were added 1.01 g. of 50% sodium hydride dispersion in oil. The dispersion was washed free of oil by repeated treatments of petroleum ether under argon. Most of the petroleum ether was removed with a syringe and the last traces removed by blowing with argon. Dimethylformamide (70 ml) was added and the suspension heated to 70°–80° C. To the stirred suspension there was slowly added dropwise over a period of 2 hours at a temperature of 85°–90° C., a mixture of 2.1 g of N,N'-dimethyl-N,N'-bis(2-mercaptoethyl) ethylenediamine and 1.58 g. of bis-2-chloroethylsulfide in 15 ml dimethylformamide. Stirring was continued overnight at 85°–90° C. after which the solvent was removed under reduced pressure. The residue was extracted with ethyl acetate, washed three times with 5 ml portions of water and dried over magnesium sulfate. The residue was concentrated to give a brown syrup and the last traces of solvent removed under reduced pressure. The product was purified by chromatography with silica gel using ethyl acetate as the eluent to furnish compound V as a pale-colored syrup which solidified under refrigeration.

$C_{12}H_{26}N_2S_3$ requires 48.93% C, 8.89 % H, 9.51 % N and 32.66% S. Elemental analysis of the product gave 48.88% C, 8.80% H, 9.38% N and 32.51% S.

EXAMPLE V

Preparation of Compound (VI)

A 500 ml hydrogenation bottle placed in a 5° C. cooling bath was charged with 6.3 g. (30 m mol) of freshly prepared N,N'-dimethyl-N,N'-bis(2-mercaptoethyl) ethylenediamine in 35 ml of carbonate-free water. To the resulting aqueous suspension there was added rapidly, with vigorous stirring, 3 ml (60 mmol) of ethylene oxide. The bottle was stoppered tightly and the contents allowed to stir for about 8 hours at 5° C. and then for another 8 hours at 25° C. The NMR spectrum of the resulting aqueous solution showed six major lines expected for the desired ligand (compound (VI) accompanied by 15–20% of unidentified impurities. Removal of the solvent under reduced pressure gave a colorless syrup which was dissolved in 75 ml of dichloromethane, washed with two 5 ml portions of water, dried over magnesium sulfate and concentrated to provide 6.5 g of a syrupy product. This product solidified upon being stored overnight in a refrigerator. Thin-layer chromatography on silica gel (in methanol) showed one major spot accompanied by traces of more polar impurities.

For further purification a 5.5 g sample of the crude material was stirred with 100 ml of ether until a fine, uniform suspension was formed. The suspension was kept at 0° C. for about 2 hours in an ice bath, the solid filtered, washed with four 10 ml portions of ether and dried in vacuo to give 3.7 g of the ligand (compound (VI)-a colorless solid m.p. 43°–44° C. $^{13}C$ and $'H$ NMR spectra were consistent with the assigned structure. The mass spectrum showed a weak m/e at 296 for the parent ion with a strong P+1 at 297.

To assure the removal of any last traces of impurities, a small sample of the ligand was chromatographed on silica gel using ethyl acetate-methanol mixture or dichloromethane-methanol mixture as the eluent. After chromatographic separation the product was crystallized from ethyl acetate-petroleum ether mixture at −15° C. to furnish pure ligand as colorless needle-like crystals, m.p. 44°–45° C. $C_{12}H_{28}N_2S_2O_2$ requires 48.61% C, 9.52% H, 9.45% N, 21.63% S, and 10.79% O. Elemental analysis gave 48.75% C, 9.60% H, 9.20% N and 21.53% S. NMR and mass spectral data were consistent with the desired ligand.

A film unit was prepared as follows: the light-sensitive element comprised a transparent polyester film base carrying on one surface an additive color screen of approximately 1000 triplets per inch of red, blue and green filter screen elements in repetitive side by side relationship; an approximately 4 micron thick polyvinylidene chloride barrier layer; a nucleating layer comprising 0.23 mg/ft$^2$ of palladium nuclei (as metal), 0.29 mg/ft$^2$ of gelatin, 0.35 mg/ft$^2$ of tin (as metal) and 0.47 mg/ft$^2$ of total chloride (associated with Pd and Sn); an interlayer of 2.21 mgs/ft$^2$ of deacetylated chitin, 0.645 mg/ft$^2$ of copper acetate (dihydrate), 0.178 mg/ft$^2$ of sodium acetate and 0.194 mg/ft$^2$ of alkyl phenoxy polyoxy ethylene glycol; a hardened gelatino silver iodobromo emulsion coated at a coverage of about 90 mgs/ft$^2$ of silver, 120 mgs/ft$^2$ of gelatin, 53 mgs/ft$^2$ of Dow-620 carboxylated styrene butadiene latex and 4.83 mgs/ft$^2$ of dioctyl ester of sodium succinic acid (a surfactant); and an antihalo topcoat of 300 mgs/ft$^2$ of gelatin, 175 mgs/ft$^2$ of Dow-620 carboxylated styrene butadiene latex, 0.3 mg/ft$^2$ of dioctyl ester of sodium succinic acid, 5.2 mg/ft$^2$ of pyridinium-bis-1,5(1,3-diethyl-2-thiol-5-barbituric acid) pentamethine oxanol, 7.0 mgs/ft$^2$ of 4-(2-chloro-4-dimethylamino benzaldehyde)-1-(p-phenylcarboxylic acid)-3-methyl pyrazolone-5 and 4.9 mgs/ft$^2$ of benzimidazole-2-thiol gold Au$^{+1}$ complex (as gold). The cover sheet was the same as described in Example I.

Film units as described above were processed in the same manner described in Example I. The processing compositions were prepared by adding 0.08725 g, 0.349 g and 0.689 g, respectively, of compound VI to 10 ml of the formulation described in Example I. These amounts of compound VI represent approximately $\frac{1}{8}$, $\frac{1}{4}$, $\frac{1}{2}$ and 1 molar equivalent, respectively, of the amount of silver solvent used for comparative purposes in Example I.

The transparencies were examined visually and found to be substantially free of crystals fifteen days after processing. The transparencies were stored under ambient conditions during the interim.

For purposes of comparison an identical film unit was processed in the same manner with the exception that the processing composition included 0.4061 g of a 2-alkylthioether-4,6-dihydroxypyrimidine complexing agent in place of compound VI. Crystals were visually apparent in the transparency within one day after processing.

Two identical film units were processed in a similar manner with the exception that the processing compositions were made up of the processing composition used in the comparative test mixed with, in the first instance, an equal volume of the processing composition containing 0.08725 g of compound VI and, in the second instance, an equal volume of the processing composition containing 0.1745 g of compound VI. When examined visually, fifteen days after processing, no crystals were apparent in the transparencies.

EXAMPLE VI

Preparation of Compound VII

To a 250 ml, three-neck flask equipped with a stirring bar, addition funnel, argon inlet and a rubber septum were added 3.98 g of 50% sodium hydride-oil dispersion. Most of the oil was removed by washing the dispersion with three 20-ml portions of petroleum ether under argon. 50 ml of dry tetrahydrofuran (99.9%) were then introduced into the dispersion from a syringe followed by a dropwise addition, with stirring, of 8.5 g (40 m mol) of N,N'-dimethyl-N,N'-bis (2-mercaptoethyl) ethylenediamine at a rate slow enough to keep frothing under control. The contents of the flask were allowed to stir for an additional 15 minutes and then treated with a solution of 10.96 g (80 m mol) methyl iodide in 7 ml tetrahydrofuran, added dropwise with vigorous stirring over a period of about 30 minutes. Throughout the addition, the temperature was maintained below 30° C. by occasional cooling in an ice bath. The resulting reaction mixture was allowed to stir at ambient temperature for about 14 hours. Excess sodium hydride was then destroyed with 5 ml of cold water and the solvent removed under reduced pressure.

The residue was taken up in 50 ml of ether, stirred for about 5 minutes and filtered to remove the suspended solids which were then washed with three 10 ml portions of ether. The combined ether filtrate and washings were treated with three 5 ml portions of water to remove any inorganic salts and dried over magnesium sulfate. Removal of solvent under reduced pressure gave 7.9 g of an essentially colorless thin liquid. Thin-layer chromatography on silica gel with methanol showed one major spot accompanied by some minor polar impurities.

To a solution of 7.5 g of the product in 50 ml of methanol were added 5.1 g of silver thiocyanate in small portions with vigorous stirring. Initially, the silver salt appeared to go into solution quite rapidly; but toward the end of the addition, the rate of dissolution slowed considerably. The mixture was allowed to stir for about 20 minutes after addition of the silver thiocyanate, diluted with 100 ml of methanol and filtered through Celite 542 to remove insoluble material. The filtrate was concentrated under reduced pressure to about 30 ml and stored overnight in a refrigerator. Crystals developed and were collected and recrystallized twice from methanol to provide 4.7 g of nearly colorless solid m.p. 106°–107° C. $C_{11}H_{24}N_3S_3 \cdot Ag$ requires 32.83%C, 6.01%H, 10.44%N, 23.90%S and 26.81%Ag. Elemental analysis gave 32.88%C, 5.89%H, 10.42%N, 23.72%S and 26.83% Ag. NMR spectra were consistent with the 1:1 compound VII-silver thiocyanate complex.

4.5 g of the complex were then dissolved in 50 ml of 60:40 (vol/vol) dichloromethane-ether mixture. The solution was cooled in an ice bath and treated with hydrogen sulfide gas to precipitate silver as silver sulfide. Following complete precipitation stirring was carried out for 15 minutes. The contents were then filtered through Celite 542 and the filtrate was concentrated under reduced pressure to give a clear liquid. The liquid was treated with a stoichiometric amount of aqueous tetramethylammonium hydroxide and the product was extracted with dichloromethane. The extracts were washed with water and dried over magnesium sulfate. The solvent was removed under reduced pressure, and there were obtained 2.45 g of the ligand (compound VII) as a clear, thin liquid. NMR spectra were consistent with the desired ligand.

Film units as described in Example V were processed in a similar manner with the exception that the processing compositions were prepared by adding 0.05405 g, 0.108 g and 1.081 g of compound VII, respectively, to 10 ml of the formulation described in Example I. The latter two processing compositions were cloudy indicating saturation. These amounts of compound VII correspond to approximately 1/10, 1/5 and 2 molar equivalent(s), respectively, of the amount of the silver solvent used for comparative testing in the previous examples.

When examined visually ten days after processing the transparencies did not have any apparent crystals. The transparencies were stored under ambient conditions during the interim.

For purposes of comparison an identical film unit was processed in the same manner with the exception that the processing composition included 0.4061 g of a 2-alkylthioether-4,6-dihydroxypyrimidine complexing agent in place of compound VII. Crystals were visually apparent in the transparency within one day after processing.

An identical film unit was processed with a processing composition made up of equal volumes of the processing composition used for comparative purposes and the processing composition containing 0.05405 g of compound VII. No crystals were visually apparent in the transparency ten days after processing. The transparency was stored under ambient conditions during the intermim.

Although the invention has been described in detail with respect to various embodiments thereof, these are intended to be illustrative only and not limiting of the invention but rather those skilled in the art will recognize that modifications and variations may be made therein which are within the spirit of the invention and the scope of the appended claims.

What is claimed is:

1. A diffusion transfer photographic process comprising the steps of:
   (a) exposing a positive-negative diffusion transfer film unit comprising a support carrying an additive color screen, a photosensitive silver halide emulsion layer and a silver precipitating layer through said additive color screen in imagewise fashion;
   (b) developing the exposed silver halide emulsion layer by contacting it with a photographic processing composition comprising an aqueous alkaline solution including a silver halide developing agent and a silver complexing agent, said silver complexing agent being stable in an alkaline environment, having a melting point less than about 50° C. and wherein the log of the stability constant ($\beta$) for a 1:1 complex of said silver complexing agent with silver is at least 10.5, wherein a silver complex which is soluble in said alkaline solution is formed between undeveloped silver halide and said silver complexing agent; and
   (c) transferring said silver complex to said silver precipitating layer and forming a silver image therein, wherein said process is carried out while retaining said film unit intact and without washing the unit.

2. The process as defined in claim 1 wherein said silver precipitating layer is located between said additive color screen and said silver halide emulsion layer.

3. The process as defined in claim 1 wherein said processing composition includes up to about 10 percent by weight of said silver complexing agent.

4. The process as defined in claim 1 wherein said additive color screen comprises red, blue and green filter screen elements in repetitive side by side relationship.

5. The process as defined in claim 1 wherein said processing composition includes in addition to said silver complexing agent a second silver complexing agent which does not possess all of the recited properties of said silver complexing agent.

6. The process as defined in claim 5 wherein said processing composition includes molar equivalent amounts of said silver complexing agent and said second silver complexing agent.

7. The process as defined in claim 1 wherein said complexing agent has a melting point of about 25° C. or less.

8. A diffusion transfer photographic process comprising the steps of
(a) exposing a positive-negative diffusion transfer film unit comprising a support carrying an additive color screen, a photosensitive silver halide emulsion layer and a silver precipitating layer through said additive color screen in imagewise fashion;
(b) developing the exposed silver halide emulsion layer by contacting it with a photographic processing composition comprising an aqueous alkaline solution including a silver halide developing agent and a silver complexing agent represented by a formula selected from the group consisting of

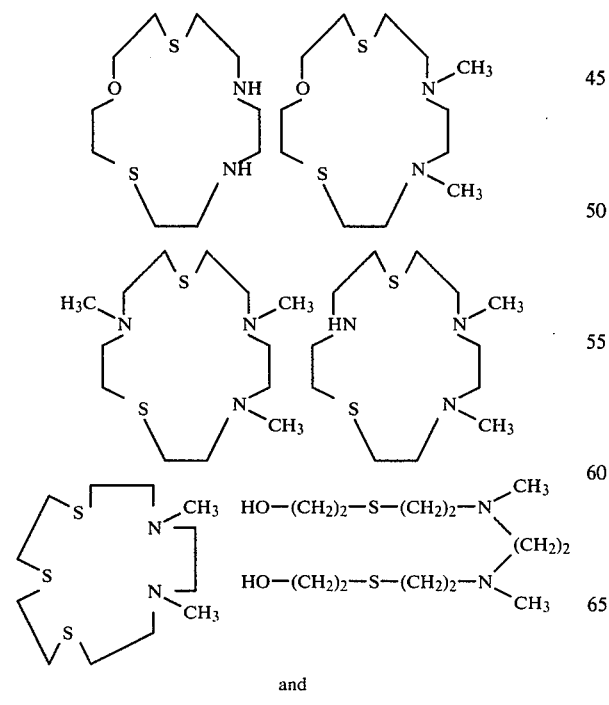

and

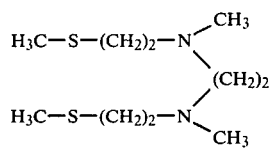

and (c) transferring said silver complex to said silver precipitating layer and forming a silver image therein, wherein said process is carried out while retaining said film unit intact and without washing the unit.

9. The process as defined in claim 8 wherein said silver complexing agent is a compound represented by the formula

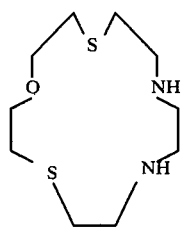

10. The process as defined in claim 8 wherein said silver complexing agent is a compound represented by the formula

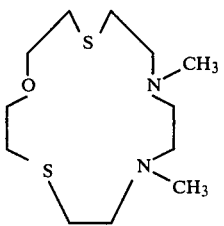

11. The process as defined in claim 8 wherein said silver complexing agent is a compound represented by the formula

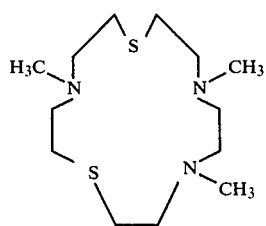

12. The process as defined in claim 8 wherein said silver complexing agent is a compound represented by the formula

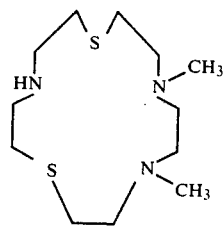
13. The process as defined in claim 8 wherein said silver complexing agent is a compound represented by the formula
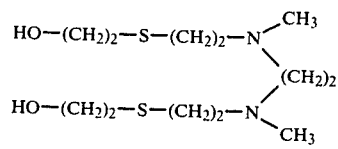
14. The process as defined in claim 8 wherein said silver complexing agent is a compound represented by the formula
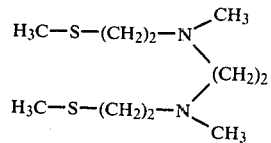
15. The process as defined in claim 8 wherein said silver complexing agent is a compound represented by the formula
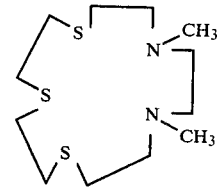
* * * * *